United States Patent
Neaud et al.

(10) Patent No.: US 10,165,789 B2
(45) Date of Patent: *Jan. 1, 2019

(54) ACEROLA POWDER FOR USE AS A SUBSTITUTE FOR ASCORBIC ACID IN THE AGRI-FOOD FIELD

(71) Applicant: DIANA NATURALS, Antrain (FR)

(72) Inventors: Fabien Neaud, Talensac (FR); Delphine Laroque, Rennes (FR)

(73) Assignee: Diana Naturals, Antrain (FR)

( * ) Notice: Subject to any disclaimer, the term of this patent is extended or adjusted under 35 U.S.C. 154(b) by 0 days.

This patent is subject to a terminal disclaimer.

(21) Appl. No.: 14/655,614

(22) PCT Filed: Dec. 26, 2013

(86) PCT No.: PCT/EP2013/078020
§ 371 (c)(1),
(2) Date: Jun. 25, 2015

(87) PCT Pub. No.: WO2014/102302
PCT Pub. Date: Jul. 3, 2014

(65) Prior Publication Data
US 2015/0327587 A1    Nov. 19, 2015

(30) Foreign Application Priority Data
Dec. 26, 2012 (FR) ..................... 12 62797

(51) Int. Cl.
*A23L 33/105* (2016.01)
*A23L 1/302* (2006.01)
(Continued)

(52) U.S. Cl.
CPC ............... *A23L 1/302* (2013.01); *A23L 2/52* (2013.01); *A23L 13/40* (2016.08); *A23L 13/428* (2016.08);
(Continued)

(58) Field of Classification Search
CPC .. A61K 2300/00; A61K 45/06; A61K 31/375; A61K 9/0095; A23V 2002/00;
(Continued)

(56) References Cited

U.S. PATENT DOCUMENTS 3,012,942 A * 12/1961 Morse ................. A61K 31/375
                                                        435/267
3,086,915 A    4/1963 Morse
(Continued)

FOREIGN PATENT DOCUMENTS

DE    10 2009 037055 A1    2/2011

OTHER PUBLICATIONS

Burdock, George A., Encyclopedia of Food and Color Additives, vol. II, CRC Press Inc., 1997, p. 1617.*
(Continued)

*Primary Examiner* — Hong T Yoo
(74) *Attorney, Agent, or Firm* — Workman Nydegger

(57) ABSTRACT

The invention concerns a powder consisting of 0.5 to 0.8% by weight of water and a dry material consisting of 88 to 95% by weight of an acerola fruit dry extract and 5 to 12% by weight of magnesium, calcium, zinc, sodium or potassium hydroxide or carbonate, the method of preparing same and the applications thereof for replacing ascorbic acid and/or the derivatives of same in food products.

14 Claims, 2 Drawing Sheets

(51) Int. Cl.
*A61K 36/185* (2006.01)
*A61K 33/08* (2006.01)
*A61K 31/375* (2006.01)
*A23L 2/52* (2006.01)
*A23P 10/40* (2016.01)
*A23L 33/15* (2016.01)
*A23L 33/16* (2016.01)
*A23L 13/40* (2016.01)
*A23L 13/60* (2016.01)

(52) U.S. Cl.
CPC ............ *A23L 13/65* (2016.08); *A23L 33/105* (2016.08); *A23L 33/15* (2016.08); *A23L 33/16* (2016.08); *A23P 10/40* (2016.08); *A61K 31/375* (2013.01); *A61K 33/08* (2013.01); *A61K 36/185* (2013.01); *A23V 2002/00* (2013.01)

(58) Field of Classification Search
CPC ........ A23V 2250/708; A23V 2250/156; A23V 2250/161; A23V 2200/30; A23V 2250/21; A23L 33/105; A23L 2/52; A23L 33/16; A23L 33/15; A23L 33/10; A23L 2/02; A23L 2/03; A23L 2/39
See application file for complete search history.

(56) References Cited

U.S. PATENT DOCUMENTS

| | | | | |
|---|---|---|---|---|
| 4,664,920 A | * | 5/1987 | Saleeb | A23L 2/39 426/250 |
| 2004/0161523 A1 | * | 8/2004 | Nair | A61K 36/45 426/640 |
| 2014/0348925 A1 | * | 11/2014 | Saura Calixto | A23L 19/09 424/489 |

OTHER PUBLICATIONS

Salunkhe, D.K, and S.S. Kadan, Handbook of Fruit Science and Technology Production, Composition, Storage and Processing, Marcel Dekker, Inc. 1995, pp. 564.*
Simopoulos, A.P. and G. Gopalan, Plants in Human Health and Nutrition Policy, Karger, 2003, pp. 67, 70, 72-75.*
International Search Report dated Jan. 27, 2014, issued in PCT Application No. PCT/EP2013/078020, filed Dec. 26, 2013.
Database FSTA International Food Information Service (IFIS), Frankfurt-Main, Germany, R. Haeussler, *Combination of Different Foods*, XP-002712223, vol. 88, No. 5, 2007, 1 page.
M. Suter et al., *Manufacture Without E-number Additives and with Reduced Salt Content*, vol. 26, No. 6, Jan. 1, 2007.

* cited by examiner

ACEROLA POWDER FOR USE AS A SUBSTITUTE FOR ASCORBIC ACID IN THE AGRI-FOOD FIELD

BACKGROUND

Acerola (*Malpighia punicifolia* L., synonymous with *Malpighia glabra* L., or *Malpighia emarginate* DC.) is a tree whose fruit is called Barbados cherry or Antilles cherry because it closely resembles the cherry.

A small tree (or shrub) with persistent foliage of the Malpighiaceae family, acerola grows spontaneously in tropical regions of South America, in particular in Peru and in the Amazon forests of Brazil and Venezuela. It is also present in the Antilles, where it is called wild cherry.

Acerola fruit contains 20 to 30 times more vitamin C than orange. This makes it one of the fruits richest in vitamin C (1000 mg to 2000 mg/100 g), after *Terminalia ferdinandiana* fruit (50 times richer than orange) and that of camu-camu (*Myrciaria dubia*) (30 to 40 times richer than orange). It is also rich in vitamin B6, vitamin B1 and vitamin A, and in flavonoids and minerals (iron, calcium, zinc, phosphorus, potassium and magnesium).

The trend towards the "natural" is well established in the food products, nutraceuticals and cosmetics markets. Naturalness is one of the keys of the success of commercial launches of products appearing on the market in recent years, all the more so in a context where the consumer now clearly perceives the risks associated with ingestion of synthetic compounds and where the laws governing the scope of the use of food additives have become more strict, as witnessed, for example, by the proposed changes to permitted additives listed in Regulation (EC) No 1333/2008 of the European Parliament and of the Council. The "clean label" nature of consumer goods is a decisive element in the purchasing act, and formulating products free of any substance unfamiliar to housewives is a great challenge that the above-mentioned industries seek to overcome.

The design of so-called "natural" consumables suggests the employment of ingredients also described as "natural". For this reason, substituting for vitamin C (generic term covering various forms, in particular ascorbic acid, isoascorbic acid or erythorbic acid, ascorbate and erythorbate salts) is a challenge that should be accepted considering the extent of its spectrum of applications. For example, replacing sodium erythorbate in cooked meats products such as injected products (cooked ham, etc.) or emulsion-type products (fine-textured sausages) with a natural ingredient that would play the same antioxidant function, if possible with fewer disadvantages, is a question raised by large number of manufacturers. There is a need, therefore, for a "natural" antioxidant to replace the various forms of vitamin C.

SUMMARY OF THE INVENTION

The Inventors have now discovered that an acerola fruit juice concentrate powder containing magnesium hydroxide can replace erythorbate in cooked meats products.

Notably, this antioxidant is natural and maltodextrin-free. Moreover, this product has the advantage of being in a powder form that is easy to use in food-processing formulations and the advantage of limiting acidification of the product.

Consequently, a first subject matter of the invention concerns a powder consisting of 0.5% to 8% by weight of water, and dry material consisting of 88% to 95% by weight of an acerola fruit dry extract, and 5% to 12% by weight of a hydroxide or carbonate of magnesium, calcium, zinc, sodium or potassium.

Preferably, the dry material of the powder of the invention consists of 90% to 94% by weight of an acerola fruit dry extract and 6% to 10% by weight of a hydroxide or carbonate of magnesium, calcium, zinc, sodium or potassium, preferably a hydroxide of magnesium.

By "acerola fruit dry extract" is meant the dry material of a product resulting from the drying of an acerola fruit juice, preferably a juice concentrate, that is, 10 to 70° Brix, preferably 45 to 55° Brix. Preferably, said juice concentrate has a vitamin C content of 3% to 24%, preferably of 15% to 21%. Preferably, said juice concentrate has an acidity of 800 to 2200 meq/kg, preferably of 1200 to 1800 meq/kg. Preferably, said juice concentrate has a pH of 2.5 to 4, preferably of 3 to 3.6.

The powder of the invention is characterised by its high vitamin C content.

Preferably, it is 30% to 40% by weight of vitamin C relative to the total weight of the powder, in a particularly preferred manner 30% to 36%, in particular 34%±3%, preferably it is 34%±2% (vitamin C analysis is carried out by reversed-phase HPLC on a Spherisorb ODS2 column or equivalent, the analysis procedure being described in European standard NF EN 14130).

The high vitamin C content of the powder according to the invention has a key importance in the nutraceuticals field, since it makes it possible to administer the recommended daily amount in a pharmaceutical form of suitable size. Moreover, in the foodstuffs industry (in particular in cooked meats), the powder of the invention, because of its high vitamin C content, can be used in a sufficiently small amount in order to limit the negative side effects associated with the incorporation of high proportions of acerola (such as acerola's taste and acidity), while providing a satisfactory amount of vitamin C in a small space (advantageous when the powder must be used in a composition of various components with limited space).

The powder of the invention features a pH range of 4 to 8. Preferably, the powder of the invention has a pH of about 4.5 to 6 (pH measured on a 10% solution in water). The lower bound of 4.5 is the pH below which it is advised not to go in order to guarantee a sufficient amount of the basic form of the ascorbic acid/ascorbate pair and to facilitate drying, even if at pH 4 to 4.5 drying remains feasible. The upper bound of 6 is a pH above which a false and undesirable "soap"-type taste may develop. However, pH values of 6 to 8 may be used if the final application is able to conceal the organoleptic defects which may develop.

Preferably, the powder of the invention comprises less than 5% by weight of water, preferably 1% to 3%.

Another subject matter of the invention concerns a method for the preparation of the powder according to the invention comprising the following steps:
  (i) mixing acerola fruit juice; a hydroxide or carbonate of magnesium, calcium, zinc, sodium or potassium; and water,
  (ii) drying to a water content of less than 8% by weight, and
  (iii) screening.

The powder of the invention is obtained by mixing acerola fruit juice, preferably concentrated; a hydroxide or carbonate of magnesium, calcium, zinc, sodium or potassium and water in selected proportions in order to allow effective drying while maximising vitamin C content.

The acerola fruit dry extract is thus present in the powder of the invention in a proportion of 88% to 95% by weight of the dry weight of the mixture.

The hydroxide or carbonate of magnesium, calcium, zinc, sodium or potassium is present in the acerola fruit juice/hydroxide or carbonate/water mixture in a proportion of 5% to 12% by weight of the dry weight of the mixture.

This amount may also be defined as a function of pH. It allows the acerola fruit juice/hydroxide or carbonate/water mixture to reach a pre-drying pH of preferably between 4.5 and 5.

As shown in FIG. 2, magnesium, calcium, zinc, sodium or potassium hydroxide or carbonate levels below 5% lead to a loss of drying efficiency and of yield. Similarly, magnesium, calcium, zinc, sodium or potassium hydroxide or carbonate levels above 12% lead to the appearance of a "soap" taste unsuited for use in food processing and to a decrease in vitamin C content resulting from a lower proportion of acerola fruit dry extract.

The amount of water of the acerola fruit juice/hydroxide or carbonate/water mixture is adjusted in order to obtain a 20 to 35° Brix mixture, preferably 30° Brix.

This mixture is then dried, preferably by spray drying or vacuum drying or any other means that guarantees that a completely soluble product will be obtained. Certain conventional methods used in the context of the manufacture of dry products, such as freeze-drying, for example, are likely to produce powders of granular or heterogeneous appearance that are associated with the generation of turbidity or insolubles after dissolution. This is shown in Example 1. Obtaining an especially soluble powder allows better release of the vitamin C and the other active components of acerola fruit and thus better application efficacy, which will broaden the application spectrum of the powder to numerous foods or food compositions. Conversely, obtaining a powder having lower solubility has consequences for the application potential of this powder, which cannot be incorporated into certain products homogeneously or without modifying the texture thereof.

The powder obtained is then screened, packaged and stored.

An acerola (*Malpighia punicifolia* L. or *Malpighia glabra* L. or *Malpighia emarginata* DC.) fruit juice concentrate is typically used as the raw material to design the powder of the invention. However, the method used to obtain the powder of the invention may also include the step of manufacturing acerola fruit juice concentrate by grinding and pressing acerola fruits and then concentrating the juice thus extracted according to conventional methods for obtaining plant juice concentrates, in particular including steps such as cooking, pasteurisation, decanting, centrifugation, filtration and ultrafiltration, enzyme treatment, fermentation, etc. These steps, in particular the enzyme treatment and fermentation steps, may improve the properties of the powder according to the invention, such as sensory profile or vitamin C content. In an optimal embodiment of the method, the raw material used is an acerola fruit clarified juice concentrate of about 45 to 55° Brix, preferably 50° Brix, with a vitamin C content of about 17% (15% to 21%, more broadly), acidity of 1200 to 1800 meq/kg and pH of about 3.5 (3 to 3.6, more broadly).

The optionally-concentrated acerola fruit juice is stored in frozen form so as to limit loss of vitamin C.

The inventors discovered in an advantageous manner that the powder according to the invention is a natural alternative to ascorbic acid and to erythorbate. While providing an effective and natural amount of vitamin C, the powder according to the invention has physicochemical features (pH, solubility, etc.) and sensory features (colour, taste, acidity, etc.) particularly suited to food-processing applications, in particular processed meat products. Examples 2 and 3 illustrate the advantage of the powder of the invention relative to ascorbic acid, both in vitro and in application.

Another subject matter of the invention concerns a food additive or ingredient comprising a powder according to the invention.

Preferably, the food additive or ingredient of the invention is intended for cooked meats products.

The product of the invention is intended for any application typically containing ascorbic acid or derivatives thereof for purposes of protecting foods (as antioxidant, colour stabiliser, etc.). For example, it is useful in the replacement of erythorbate salts commonly employed in cooked meats products (acts in forming of the pink colour typical of such applications like cooked ham, sausages, etc.).

It is proven that the residual nitrites level in cooked meats applications is minimised in the presence of erythorbate or derivatives thereof and any form acting as a vector thereof. The presence of high nitrites contents poses a public health problem, namely generation of nitrosamines in vivo and cancer risks attributed thereto. The powder of the invention also helps reduce the formation of endogenous nitrosamines. Indeed, the cumulative effect of vitamin C and other nutrients present in the powder of the invention (in particular polyphenols) help to reduce the residual nitrites content in cooked meats and thus to limit the formation of nitrosamines in vivo.

The product of the invention can also be used as an agent for treating flour (as antioxidant, effect on bread quality such as volume, crumb texture, crust appearance, etc.) and to replace ascorbic acid and derivatives thereof in applications such as beverages (fruit juices, nectars, noncarbonated flavoured beverages, etc.), bakery products (bread, brioches, sweet pastries, etc.), cereal products, soups, sauces, snacks, prepared dishes, fruit-based processed products (compotes, jams, etc.), etc. These products generally employ vitamin C in amounts varying from 50 to 500 ppm, even if lower or higher amounts may be useful according to the application concerned (0-1500 ppm). For example, the product was successfully tested in meat matrices (cooked pork ham, ground pork, frankfurter-type sausages) at concentrations varying from 170 to 510 ppm ascorbic acid equivalent, in brioche-type matrices in amounts of 50 and 150 ppm ascorbic acid equivalent, in fruit juices, fruit compotes and sugared fruits in amounts of 200 and 750 ppm ascorbic acid equivalent. In all these applications the feasibility of substituting ascorbic acid or derivatives thereof with acerola powder was validated, and adding the product of the invention was even associated with the development of secondary benefits (effect on taste, texture, appearance, etc.). For example, substituting for ascorbic acid or derivatives thereof with acerola powder makes it possible to enhance the fruity taste of fruit juices, to develop in ham a characteristic colour that is preferred over a sodium erythorbate control, to maintain over time the soft texture of a brioche, etc. These effects can be explained by the fact that the powder of the invention provides not only vitamin C but also other active compounds, such as carotenoids, polyphenols and organic acids (in particular malic acid), playing a role in the matrix, alone or synergistically with vitamin C.

Another subject matter of the invention concerns a food or food composition comprising a powder according to the invention or a food additive or ingredient according to the invention. Preferably, this food or food composition is a beverage, a bakery product, a cereal product, a soup, a sauce, a snack, a prepared dish, a fruit-based processed product or a cooked meats product.

Another subject matter of the invention concerns the use of a powder according to the invention to replace ascorbic acid and/or derivatives thereof in food products. For example, the powder of the invention may be used to replace erythorbate in cooked meats products.

Indeed, the product of the invention is particularly suited to neutral applications because of its acid to neutral pH. This property limits changes in texture.

DETAILED DESCRIPTION OF THE PREFERRED EMBODIMENTS

Examples

Example 1—Production and Solubilisation Properties of a Powder According to the Invention i. Production of a Powder According to the Invention Taking into account the features of the acerola fruit juice concentrate employed (50° Brix, 17% vitamin C), the pH of the mixture was stabilised at 4.5 with 92% acerola fruit juice concentrate and 8% magnesium hydroxide (percentages expressed relative to the dry material).

The amount of water to be added was then calculated so as to obtain a ° Brix value for the acerola fruit juice concentrate/magnesium hydroxide/water mixture of 30° Brix.

Consequently, the following formulation was prepared according to the method below:

| Raw material | Recipe (% of dry material) | pH | Amount employed (kg) |
|---|---|---|---|
| Acerola fruit juice concentrate | 92 | 3.01 | 420 |
| Magnesium hydroxide | 8 | 14 | 15 |
| Water | — | 7.61 | 300 |

The materials were mixed in a vat and the mixture was spray-dried (inlet temperature 160° C., outlet temperature 86-88° C.). The powder was screened with a 650 µm mesh and packaged in aluminium bags.

The yield obtained is 73.5% and productivity is about 84 kg/h.

Figure 1:
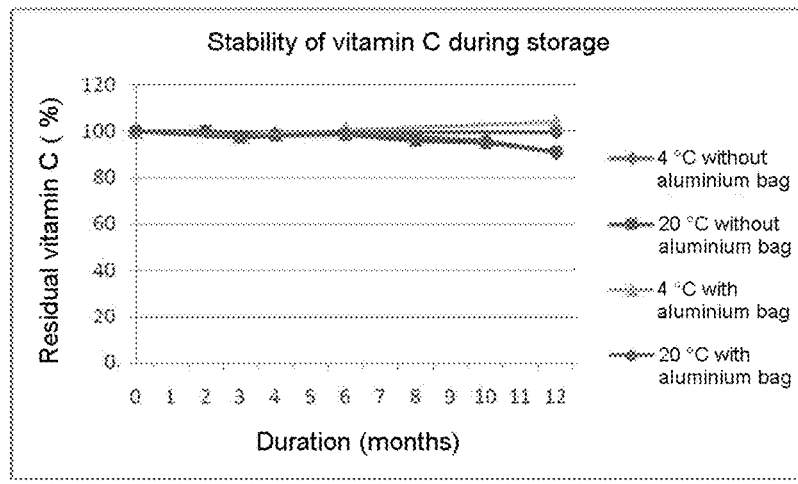
FIG. 1: Change in vitamin C content of the powder of the invention during storage at 4° C. or 20° C. in an aluminium bag or without an aluminium bag.

The powder is characterised by a vitamin C content of 36.7% by weight of the total weight of the powder, which is stable over time as shown by the ageing test applied to the powder (see FIG. 1).

The product has excellent solubility (absence of a pellet visible to the naked eye after dissolution of the powder at a concentration of 10% by weight of the total weight of the powder in water and then centrifugation at 10,000 g for 10 minutes) and the solution obtained is bright and clear.

ii. Effect of Magnesium Hydroxide Content in the Powder of the Invention

In order to illustrate the importance of magnesium hydroxide content in the powder of the invention, spray-drying tests were carried out with various levels of Mg(OH)2 (here, pilot-stage tests).

Figure 2:
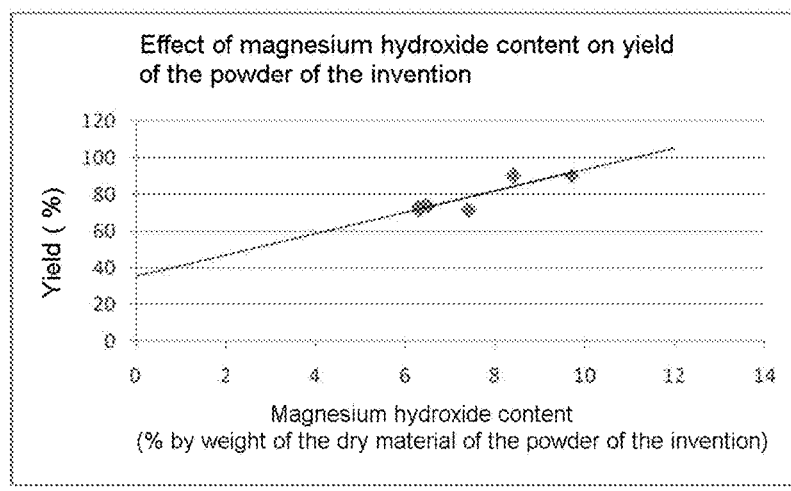
FIG. 2: Demonstration of the importance of magnesium hydroxide content on the yield of the powder of the invention.

As the graph in FIG. 2 proves, the yield of the powder of the invention decreases with decreasing amounts of magnesium hydroxide, reaching values below 65% (poor yield) with a magnesium hydroxide content of 5% by weight (content expressed relative to the dry material of the powder of the invention).

iii. Solubilisation Properties of a Powder of the Invention

In order to show the lower solubility of a freeze-dried acerola powder, solubilisation tests were performed on the sprayed powder of the invention compared with a freeze-dried powder. The results are presented below in Table 1.

TABLE 1

Solubilisation tests of acerola powders obtained by means of two different drying methods (spraying for the powder of the invention and freeze-drying)

| Sample (diluted to 10% in water) | Insoluble materials (%) |
|---|---|
| Acerola powder of the invention | 1.8 ± 0.3 |
| Freeze-dried acerola powder | 5.7 ± 0.1 |

These tests clearly show the lower solubility of the freeze-dried powder (quantification of insoluble materials presented in Table 1). About three times more insoluble compounds are generated from a 10% solution of freeze-dried powder. Furthermore, the appearance of a pellet visible to the naked eye is noted in the case of the test performed with the freeze-dried powder, which is not the case for the test performed with the powder of the invention.

This criterion may act to curb the use of the product in bright and clear products (beverages, for example). Furthermore, it may be assumed that in a freeze-dried powder characterised by many insoluble particles when in solution, vitamin C is less available and is less effective in terms of the effects attributed thereto (role as antioxidant, stabiliser, etc.). On the other hand, the spectrum of use of the powder of the invention (obtained by spraying) is not subject to this constraint.

Example 2—Antioxidant Potential of the Powder of Example 1 Versus Ascorbic Acid

Tests performed in vitro illustrate the properties of the powder of the invention in comparison with the single effect of ascorbic acid. The table below shows that the powder of Example 1, in comparison with ascorbic acid, has a greater antiradical and antioxidant activity than that of equivalent concentrations of ascorbic acid.

TABLE 2

Evaluation of the antioxidant power of
acerola powder versus ascorbic acid

| Method | Powder of the invention | Ascorbic acid |
| --- | --- | --- |
| Antiradical activity (% of trapping of the free radical DPPH at the fixed concentration of 0.44 mg/ml ascorbic acid eq) | 90.1 | 70.6* |
| Overall antioxidant power (g/100 g of product in ascorbic acid eq) | 58 | 34 |

*Ascorbic acid tested in combination with $Mg(OH)_2$ in the proportions present in the powder of the invention.

Example 3—Efficacy in a Food Application of the Powder of the Invention as a Natural Substitute for Ascorbic Acid and Derivatives Thereof i. Natural Alternative to Sodium Erythorbate used in Cooked Meats Products The powder of Example 1 was tested in a cooked pork ham matrix ("injected" product model). It was diluted in a brine intended for injection into the cooked meats product so as to reach a final concentration in the finished product of 425 ppm of vitamin C. A control prepared under the same conditions but comprising sodium erythorbate incorporated so as to reach equivalent erythorbate concentrations was also used as a comparison product. The ham was vacuum-packed after being sliced, then stored at 4° C. for up to 12 weeks.

The table below summarises the product features obtained with sodium erythorbate and with the powder of Example 1, respectively.

TABLE 3

Features of hams containing the acerola powder of the invention
versus sodium erythorbate after 12 weeks of storage at 4° C.

| | Powders of the invention | Sodium Erythorbate |
| --- | --- | --- |
| Yield after cooking (%) | 91.87 | 92.19 |
| Sensory evaluation | Colour: very good result in terms of colour, pink, typical of ham, product preferred over the control<br>Texture: very good result, texture judged better compared with the control, firm<br>Taste: smoky, salty, attributes of cooked meats products | Colour: pink, typical of ham<br>Texture: typical of ham<br>Taste: smoky, salty, typical of ham |
| Total aerobic mesophilic flora (CFU/g) | <10 | <10 |

The tests performed show the possibility of replacing sodium erythorbate with the product of the invention, the hams thus obtained being as appreciated as, even more appreciated than, the control. Furthermore, the fact of substituting the traditionally used additive with the natural powder of the invention does not have an impact on the yield or on the microbiological quality of the product.

Similar tests of substituting for sodium erythorbate with the powder of Example 1 in amounts for reaching 300 ppm of erythorbate or of vitamin C in the finished product were also performed in frankfurter-type sausages ("emulsion"-type fine-texture product model). The results are just as satisfactory, as shown by the texture analyses, the microbiological analyses, the oxidation level analyses and the sensory evaluation conducted throughout the life of the product (storage at 4° C. for 3 weeks). Benefits may again be observed in the presence of the powder of the invention compared with the control. In particular, the product of the invention is able to limit the loss of organoleptic intensity observed during storage of the control containing sodium erythorbate.

ii. Natural Alternative to Ascorbic Acid used in Bakery Products

Figure 3:
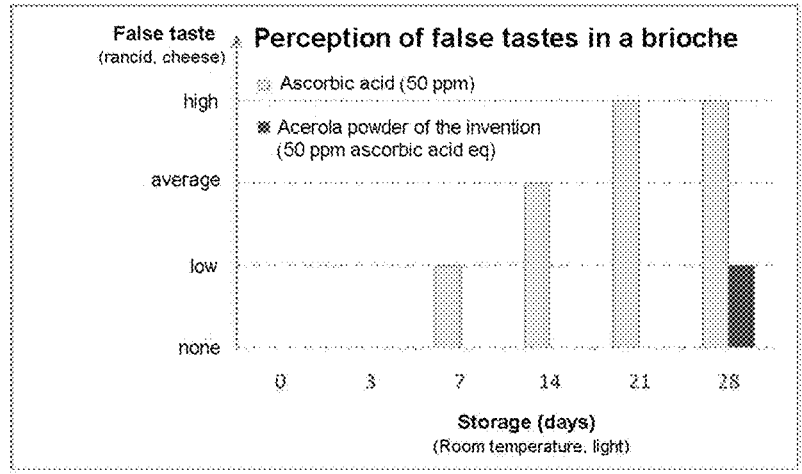
FIG. 3: Effect of replacing ascorbic acid with the powder of the invention on the sensory profile of a bakery matrix.

The powder of Example 1 was also incorporated into other types of applications, in particular brioche-type bakery products at concentrations reaching 50 or 150 ppm of vitamin C in the finished product. The feasibility of substituting for ascorbic acid introduced in the same amounts is proven once again. The powder of the invention even has advantages compared to the ascorbic acid control, slowing the appearance of false tastes which may develop during storage at room temperature, as shown in FIG. 3.

Figure 4:
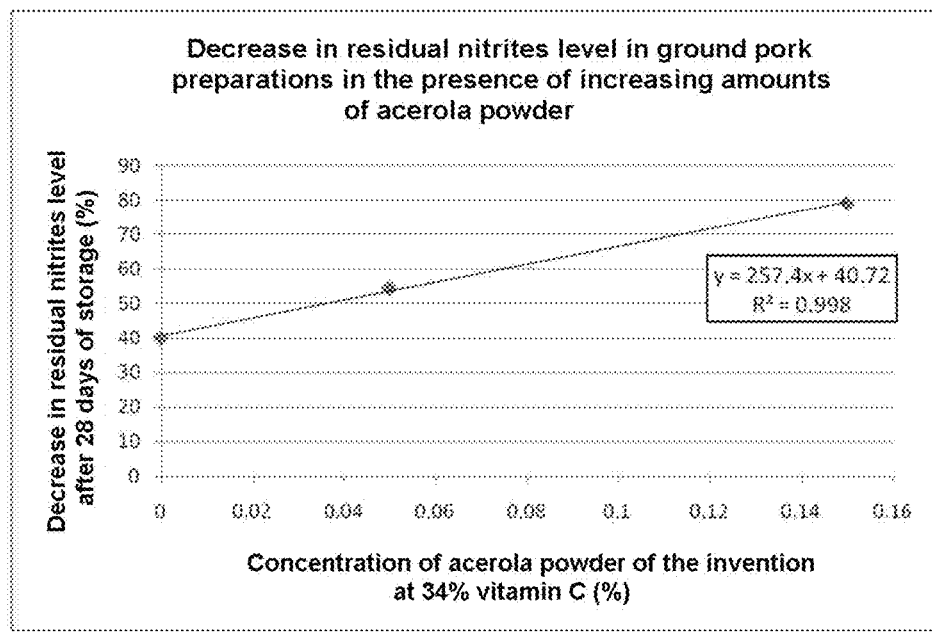
FIG. 4: Effect of increasing concentrations of the powder of the invention on the percentage decrease in nitrites present in ground pork preparations after 4 weeks of storage at 4° C.

Example 4—Effect of the Product of the Invention on Decrease in Residual Nitrites Level in a Cooked Meats Application The powder of the invention was incorporated into a ground pork-based formulation at concentrations reaching 170 ppm and 510 ppm of vitamin C (at concentrations of 0.05% and 0.15% by weight of powder relative to the weight of the fresh meat preparation, respectively). The preparations were vacuum-packed in the form of 80 g "hamburger steak"-type portions, cooked and stored at 4° C. for up to 4 weeks. The nitrites level present in the meat preparations was analysed regularly during storage. The graph in FIG. 4 presents the results obtained at the end of 4 weeks of storage.

The tests performed show the linear relationship between percentage decrease in residual nitrites level and amount of powder of the invention incorporated into the matrix. Notably, a lower residual nitrites level is associated with a lower level of nitrosamine formation in vivo and thus with a lower risk of development of cancers of the digestive system.

The invention claimed is:

1. A powder consisting of:
   0.5% to 8% by weight of water, relative to the total weight of the powder; and
   a dry material consisting of:
   88% to 95% by weight of dried acerola fruit juice, relative to the total weight of the dry material; and
   5% to 12% by weight of a hydroxide or carbonate of magnesium, calcium, zinc, sodium or potassium, relative to the total weight of the dry material,
   wherein the dried acerola fruit juice provides the powder with a vitamin C content of 30% to 40% by weight relative to the total weight of the powder.

2. The powder according to claim 1, containing natural vitamin C content of 34%±3% by weight, relative to the total weight of the powder.

3. The powder according to claim 2, wherein the natural vitamin C content is 34%±2%, by weight, relative to the total weight of the powder.

4. The powder according to claim 1, having a pH varying from 4 to 8.

5. The powder according to claim 4, wherein the pH varies between 4.5 to 6.

6. The powder according to claim 1, comprising 0.5% to 5% by weight of water, relative to the total weight of the powder.

7. The powder according to claim 6, comprising 1% to 3% by weight of water, relative to the total weight of the powder.

8. A method for preparing the powder of claim 1, the method comprising the following steps:
  (i) mixing acerola fruit juice; a hydroxide or carbonate of calcium, zinc, sodium or potassium; and water,
  (ii) drying the mixture to a water content of 0.5% to 8% by weight, relative to the total weight of the powder, and
  (iii) screening the powder obtained.

9. The method according to claim 8 wherein the drying is carried out by spraying.

10. A food additive or ingredient comprising the powder of according to claim 1.

11. A food or food composition comprising the food additive or ingredient according to claim 10 combined with a food component.

12. A food or food composition comprising the powder according to claim 1 combined with a food component.

13. A method comprising:
  providing a powder, the powder consisting of:
    0.5% to 8% by weight of water, relative to the total weight of the powder; and
    a dry material consisting of:
      88% to 95% by weight of dried acerola fruit juice, relative to the total weight of the dry material; and
      5% to 12% by weight of a hydroxide or carbonate of magnesium, calcium, zinc, sodium or potassium, relative to the total weight of the dry material,
      wherein the dried acerola fruit juice provides the powder with a vitamin C content of 30% to 40% by weight relative to the total weight of the powder; and
  applying the powder to a food product to replace ascorbic acid and/or derivatives thereof.

14. The method of claim 13 wherein the powder is applied to a charcuterie product to replace erythorbate.

* * * * *